(12) United States Patent
Babcock

(10) Patent No.: US 6,740,110 B2
(45) Date of Patent: May 25, 2004

(54) METHOD AND DEVICES OF INFLAMMATION CONTROL, AND THERAPY

(76) Inventor: David A. Babcock, 440 Sky Oaks Dr., Angwin, CA (US) 94508

(*) Notice: Subject to any disclaimer, the term of this patent is extended or adjusted under 35 U.S.C. 154(b) by 58 days.

(21) Appl. No.: 10/155,622

(22) Filed: May 22, 2002

(65) Prior Publication Data

US 2004/0024436 A1 Feb. 5, 2004

Related U.S. Application Data (60) Provisional application No. 60/292,819, filed on May 22, 2001.

(51) Int. Cl.$^7$ .................................................. A61F 7/00
(52) U.S. Cl. ........................................ 607/108; 607/104
(58) Field of Search .................... 607/96, 104, 108–112

(56) References Cited

U.S. PATENT DOCUMENTS

| | | | | |
|---|---|---|---|---|
| 787,920 A | | 4/1905 | Hofmann | |
| 2,415,455 A | * | 2/1947 | Barnes et al. | 607/104 |
| 2,726,658 A | | 12/1955 | Chessey | 128/400 |
| 2,885,189 A | | 5/1959 | MacCracken | 257/215 |
| 2,930,594 A | | 3/1960 | MacCracken | 257/306 |
| 3,154,926 A | | 11/1964 | Hirschorn | 62/3 |
| 3,867,939 A | | 2/1975 | Moore et al. | 128/254 |
| 3,908,655 A | | 9/1975 | Lund | 128/256 |
| 3,916,911 A | * | 11/1975 | Sauder et al. | 607/104 |
| 4,123,511 A | | 10/1978 | Heintze | 424/46 |
| 4,329,997 A | | 5/1982 | de Yampert et al. | 128/402 |
| 4,680,309 A | | 7/1987 | Maurer | 514/499 |
| 4,691,762 A | | 9/1987 | Elkins et al. | 165/46 |
| 4,745,922 A | * | 5/1988 | Taylor | 607/104 |
| 4,887,326 A | | 12/1989 | O'Brien et al. | 5/421 |
| 5,344,437 A | | 9/1994 | Pistay | 607/109 |
| 5,372,608 A | | 12/1994 | Johnson | 607/104 |
| 5,411,541 A | | 5/1995 | Bell et al. | 607/104 |
| 5,486,206 A | | 1/1996 | Avery | 607/104 |
| 5,507,792 A | | 4/1996 | Mason et al. | 607/104 |
| 5,562,604 A | | 10/1996 | Yablon et al. | 601/148 |
| 5,697,961 A | | 12/1997 | Kiamil | 607/108 |
| 5,913,885 A | | 6/1999 | Klatz et al. | 607/104 |
| 6,030,412 A | | 2/2000 | Klatz et al. | 607/104 |
| 6,171,606 B1 | | 1/2001 | Lyons | 424/402 |
| 6,178,562 B1 | | 1/2001 | Elkins | 2/458 |
| 6,183,501 B1 | | 2/2001 | Latham | 607/109 |

OTHER PUBLICATIONS

Aricle by A.S. Gissen entitled "Copper: The Maligned Mineral" which first appeared in Apr.–Jul./Aug. '94 issues of VRP's Newsletter. This article discusses needs of correct copper balance, and reasons for deficiency.

* cited by examiner

Primary Examiner—Roy D. Gibson (57) ABSTRACT

A portable device of coiled copper tubing and copper sheet metal construction that is ergonomically designed to provide a combination of beneficial practices into one more effective method, and devices for inflammation control, injury immobilization and therapy. The combination of copper in contact with the skin, the ability to perform hot and cold treatments, or steady cold treatments for an extended period of time, and the ability to provide adjustable ergonomic support provide an improve method and devices for the treatment of injuries, aches, and pains.

22 Claims, 7 Drawing Sheets

METHOD AND DEVICES OF INFLAMMATION CONTROL, AND THERAPY

CROSS-REFERENCE TO THE RELATED APPLICATION

This application claims the benefit of Provisional Patent Application Ser. No. 60/292819 filed May 22, 2001.

BACKGROUND-FIELD OF INVENTION

This invention relates to a method and devices that provide an improved way to reduce inflammation, and a simpler way to administer therapy, by combining some known concepts into more effective devices.

BACKGROUND-DESCRIPTION OF PRIOR ART

A need exists for an improved method and device for the immobilization of an injured person, controlling inflammation after traumatic injury, for externally controlling blood circulation and for the encouragement of muscle relaxation during stabilization and recovery. After an individual has received a traumatic neck or spinal injury, often there is more damage caused by the resulting inflammation and tightening of the muscles than was caused by the initial injury itself. Countless individuals have survived the initial impacts causing their injury, only to succumb to the inability of their health care providers to manage the inflammation and tightening of muscles, which irreparably damages the spinal chord. Medications have been developed which attempt to combat these conditions. However, these are not effective enough, and it has been found that the side effects of these could be causing as much harm as good. Often as conditions begin to get out of hand, in an effort to do something, surgeons are called upon to relieve the pressure on the spine by surgically cutting strategic pressure points. Often this can cause further inflammation as the body attempts to combat the invasive procedure. If the individual does survive, they are faced with recovery from the initial injury, the resultant inflammation, and the invasive procedure. Studies have shown that the application of cold temperatures does help to reduce the onset of this inflammation. Ideally, as the application of cold temperatures should be a simple, basic operation, and as early application enhances its effectiveness, it should begin in the field prior to arrival at the medical facility.

U.S. Pat. No. 6,183,501 has attempted to provide a solution to this problem. It is of a design similar to fairly common C-collars, however this one provides cavities that can contain temperature controlling substances. It falls short though, in two ways. First, it's design of larger pieces would make it more difficult to custom shape the device to contact the user's skin in areas that would be most beneficial to user. Secondly, being made of material other than copper, the temperature distribution would not be as even. This and the distance from the skin reduce its effectiveness. U.S. Pat. No. 6,030,412 also attempts to remedy these temperature applications considerations in a device that can be used in the field, but this also has a distance between critical areas that would require much lower temperatures to be effective. Neither of these devices provides the benefits of copper, as expanded upon below, which include encouragement of the muscles to relax, that the devices used in this method provide. Neither provides the type of beneficial ergonomic adjustable support the devices used in this method provide.

U.S. Pat. No. 5,913,885 is also designed to combat this inflammation problem using cold temperatures. However, this device does not allow for as much flexibility in the neck region, and does not include the benefits of copper.

U.S. Pat. No. 3,908,655 is also designed to combat this inflammation problem using cold temperatures, but this relies on air to carry the temperature, is much bulkier so it would be difficult to move around, more costly to produce, and it also does not include the benefits of copper.

U.S. Pat. No. 4,691,762 uses a portable temperature control system, part of which would work well in combinations with the present invention. This patent describes a personal temperature control system that is designed more for environmental comfort of the user in the form of a garment. This would work for certain medical conditions requiring temperature control. In one form, it simply circulates coolant fluid through a temperature exchange coil that is submerged in ice water, then back through the garment. But the garments do not include the advantages of copper or provide support. U.S. Pat. No. 2,930,594 shows a temperature exchange device that simply uses a standard water faucet as a source of temperature transporting substance. The temperature can be changed by changing the faucet settings, while the small amount of returning water simply goes down the drain. This has been found to be very adequate in conjunction with the present invention as long as the water is either cold or warm enough depending on the type of treatment. U.S. Pat. No. 5,372,608 uses the bodies own temperature to circulate the fluid. However none of these provide the type of support nor benefits of copper the present invention provides.

Often after an injury, the vertebrae in the neck begin to straighten into a line as seen from the victim's side. The neck is supposed to have a curve as seen from the side. As the neck straightens, nerves in between the vertebrae are pinched, and the patient experiences any of many different kinds of discomfort. For many years, Chiropractors have encouraged the use of a towel roll while laying down to help the neck relax in, retain, or return to this curved posture. This has been found to provide much relief. However, at times, due to the patient's condition and extent of injury, they may not at first be able to tolerate very much curving support from the towel roll. In these cases, the towel roll is simply unrolled to a smaller size until a little extra support is achieved. Then over a period of time as the patient heals and becomes accustom to this smaller roll, the towel is slowly rolled up further and further to increase the curve in the neck until it reaches normal. The towel roll is great for the shape, but often a cold surface adds further relief. The use of a towel roll, covered with a gel ice pack can help provide both, but this stays cool only a short while, and often the gel is pushed out of the most supported areas and the cooling effect doesn't last as long in those areas. U.S. Pat. Nos. 4,887,326, 5,697,961, 5,344,437, use a pouch that can contain the ice or heated fluid. However these do not provide a continuos cold temperature for an extend time as is desirable with sever injuries, are harder to regulate the shape of, and do not include the benefits of copper, thus making them less effective.

Medical people have, for many years, known the benefits that the muscles can receive from the alternating of hot and cold. As described below, the devices the present invention uses for implementation, one is able to easily have hot and cold treatments administered while they are relaxing comfortably with out the hassle of changing ice packs to other types of heated articles. The ability to have the temperature automatically changed from hot to cold is a great benefit for therapy purposes. Studies indicate that people having trouble with swollen disc shouldn't use heat. Though providing temporary relief, the heat only causes the discs to swell further, additional aggravating the discomfort in the long run. However, it is also commonly accepted that the muscles that are injured benefit from having hot and cold treatments. A dilemma arises when both are experiencing trouble in the same area. When this occurs, the need to change temperatures quickly becomes apparent. The present invention performs this quick change faster and more effectively than prior art. Devices that hold their temperature, by relying on the volume of the material at desire treatment temperature, have to be changed. Devices that circulate a temperature carrying substance, but are constructed out of material other that copper, do not relay the change in temperature as quickly.

Research has shown that after a limb such as a leg is injured, if the injured area is quickly cooled and maintained in this cool condition, the recovery takes place quicker. However, with many of the commonly used splints, the limb is first immobilized with some type of stiff material such as hard plastic, stiff cardboard, or a flexible wire mesh. Then this immobilizing material and the limb are wrapped with a cloth material of varying consistencies, to keep them in place over the immobilizing material. Cold ice packs can be administered over the wrapping material, however this material greatly reduces the amount of cool temperature that actually reaches the injured area of the limb. U.S. Pat. No. 4,329,997 does apply cold to the injured limb; however, it is bulky and would greatly complicate the transfer of the patient from one gurney to another, or from a gurney to a hospital bed. If the water were to be let out of the device for this transfer, immobilization of the limb would be lost. This device also fails to provide the benefits of copper.

Copper is a great conductor of thermal energy; it has tremendous benefits as an anti-inflammatory and muscle relaxant and also conducts electricity very effectively. When copper is next to the skin, the skin absorbs a small amount of the copper. Copper is a natural mineral that our bodies need. Wearing copper bracelets has become popular with golfers that have experienced trouble with their wrists. Many claim that they have had relief in other areas of the bodies as well. A number of researchers have been studying the benefits of copper. U.S. Pat. Nos. 4,680,309, 6,171,606 discuss some of these benefits as do studies such as one preformed by the Vitamin Research Products, Inc. "Copper: The Maligned Mineral" is an article that first appeared in the April-July/August, 1994 issues of the magazine VRP's Newsletter. This and other studies show that the copper is drawn to the area of the inflammation by the body to help combat the inflammation. They point out that the introduction of a small amount of copper into the body actually reduces the chances of arthritis setting in. As well as conducting temperature, copper also is good at conducting electricity. By being in contact with the skin, it helps to route and balance the electric flow of the body. Muscles that are too tight are receiving too much electric energy. The copper bridging the nerve endings on the skin helps to reroute the electric energy in the body reducing the amount sent to muscles that are over tightened thus helpings them to relax further aiding in the stabilization, recovery and healing process. U.S. Pat. No. 4,680,309, does introduce the copper to the skin in or near the location of the discomfort. However, it does not include the added benefits of temperature treatments, therapeutic adjustable ergonomic shaping, or injury immobilization.

SUMMARY

The present invention combines the useful concepts described above into one more effective method of achieving relief from inflammation, tight muscles, and pain. Thus, by using the combinations of temperature treatments, the benefits of copper and the ability to adjust the shape of the supporting device, the present invention provides a complete and superior treatment for patients.

Objects and Advantages

Accordingly, several objects and advantages are:

(a) Extreme temperatures are not as important. Therefore less energy is required to operate devices of this method. The use of cold water, or conversely very warm water, is adequate for most treatments. As the copper conducts thermal energy so well and when used in the optimal position directly in contact with the skin, extremely cold fluid or gasses are not as essential as with some of the prior art. This transfer of thermal energy is so effective that when used for hot treatment while a regular household's water tap is supplying the thermal energy source, care must be taken not to burn the skin. With prior art devices that use less conductive material in contact with the skin, these materials act as insulation requiring more energy to provide treatment through it to the skin. The ability of the devices of this method to conserve energy enables them to be operated less expensively, and more portably. As one skilled in the art would see, the devices the present invention uses to fulfill its objectives could easily be adapted to work in combination with and improve upon many different temperature exchange systems to fulfill its purposes.

(b) The ability to adjust the shape of the devices of this method provides improved means of treatment. As with the changing of the size of the towel roll, as mention above, the ability to more easily change the ergonomic shape of the devices of this method provide a all around more effective treatment by making the devices of this method more custom fit. This custom fit that is more suited to the patients condition is less apt to aggravate the patient's condition by attempting to shape the injury in an undesirable way. But rather aids the patient by encouraging the correct shape while making changes in a more acceptable way. While some of the prior art would require re-machining, or multiple devices to accomplish this, the devices of this method can simply be adjusted as needed. As one skilled in the art can see, an adjustable device that supports and helps the neck maintain, or return to the natural curve that it is suppose to have has many advantages (c) By being more easily changed from cold to hot, the devices of this method provide an improved means of performing temperature treatments to areas where swollen joints are in the same proximity as injured muscles. When injured muscles are in the same area as swollen joints, a dilemma arises because swollen joint are best treated with cold only, and muscles are best benefited by a combination of hot and cold. The answer improved upon by the present invention lies in applying cold to the area in this condition, for a long enough time that the cold treatment has time to reach deep into the disc to reduce swelling there. Then hot should be applied for a brief time, only long enough to draw blood into the muscles, but not into the discs. Cold should be once again applied, for longer than the heat, then once again the heat and so on finishing with cold at the end of the treatment. With the devices of this method, one could easily have the treatment while laying back in a recliner. So the circulated liquid cooling and heating advantage becomes obvious. With the devices of this method, the copper helps to transmit the temperature from the fluid to the skin. Therefore, as one skilled in the art would see, the present invention is of further aid by working in combination with, and improving upon systems with automatic controls that would be suited to these temperature control requirements.

(d) The ergonomic shape of the copper while in contact with the skin helps relax muscles, and reduce swelling. This ergonomic shape allows more of the skin to be contacted, thereby allowing more nerve endings to be in contact with the copper. This contact of the nerve endings with the copper allows the electrical energy in the body to more easily stabilize, thereby helping to relax muscles that are receiving to much energy. The contact with the skin also allows the skin to absorb small amounts of copper, which in turn aid in the reduction of inflammation.

By combining the temperature control ability with the benefits of copper and the adjustable ergonomic shape of the devices of this method, the present invention provides a better therapy than is received by using anyone of the treatments alone.

REFERENCE NUMERALS

Figures 1, 2, 3:
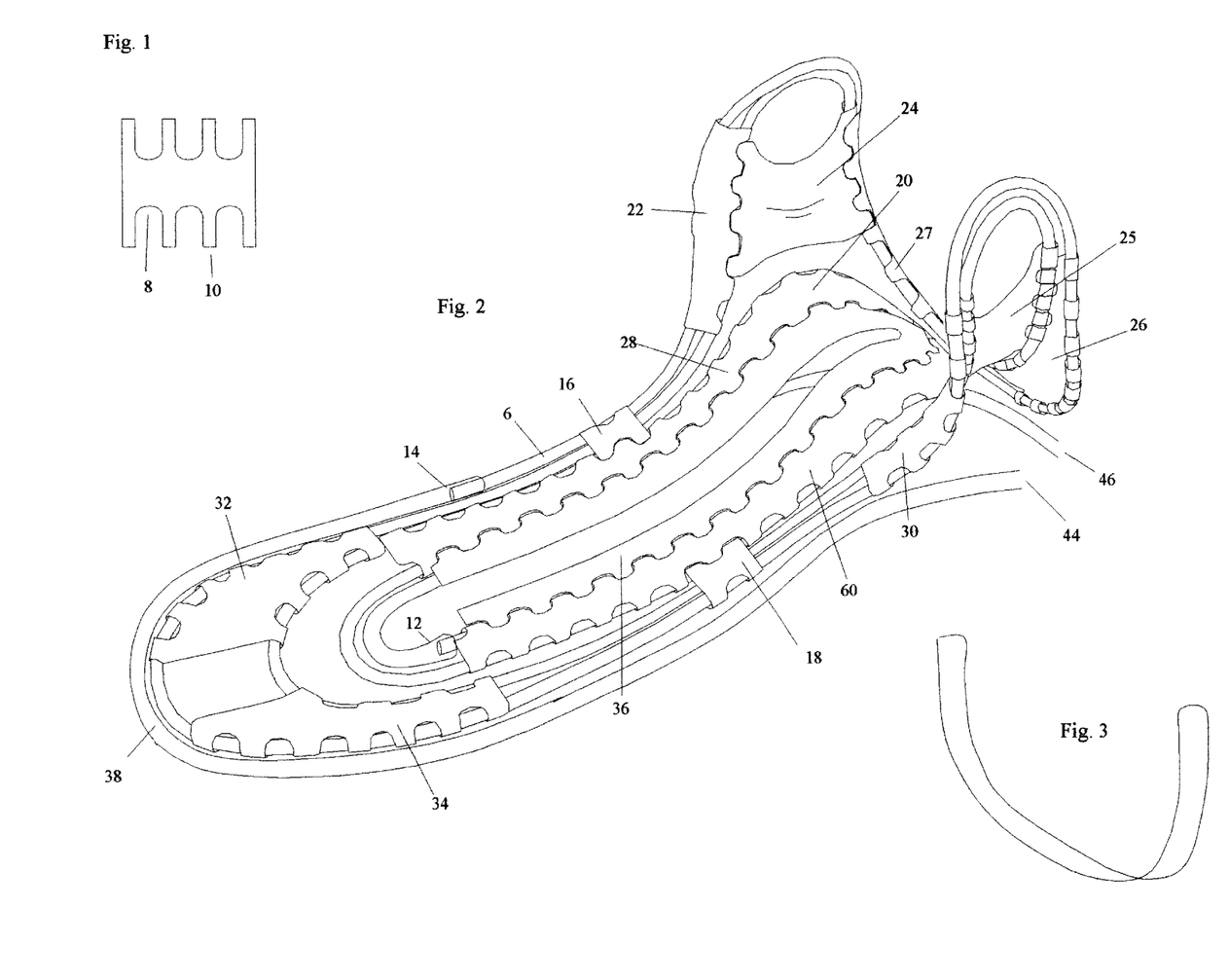
FIG. 1 is a view from directly above a sample pattern of a piece of copper sheet metal as it would look before attachment to the device shown in FIG. 2
FIG. 2 is an isometric perspective view of an ergonomically designed, copper neck and upper back supporting device as seen from its left side.
FIG. 3 is an isometric perspective view of an optional curvature pressure adjustment strap.
Figure 4A:
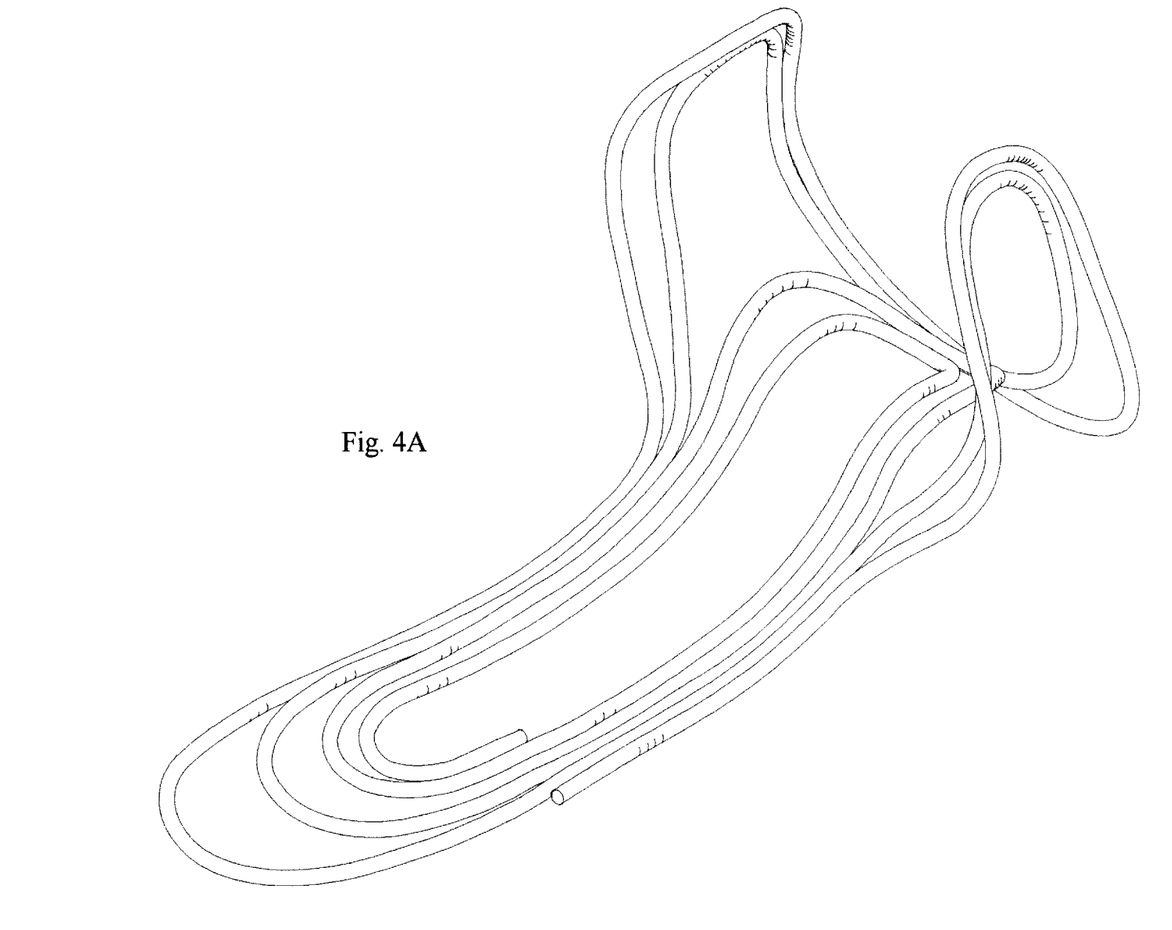
FIG. 4A is an isometric perspective view of just the copper tubing as it would appear if FIG. 2 did not yet have the copper sheet metal pieces in place.
Figure 4B:
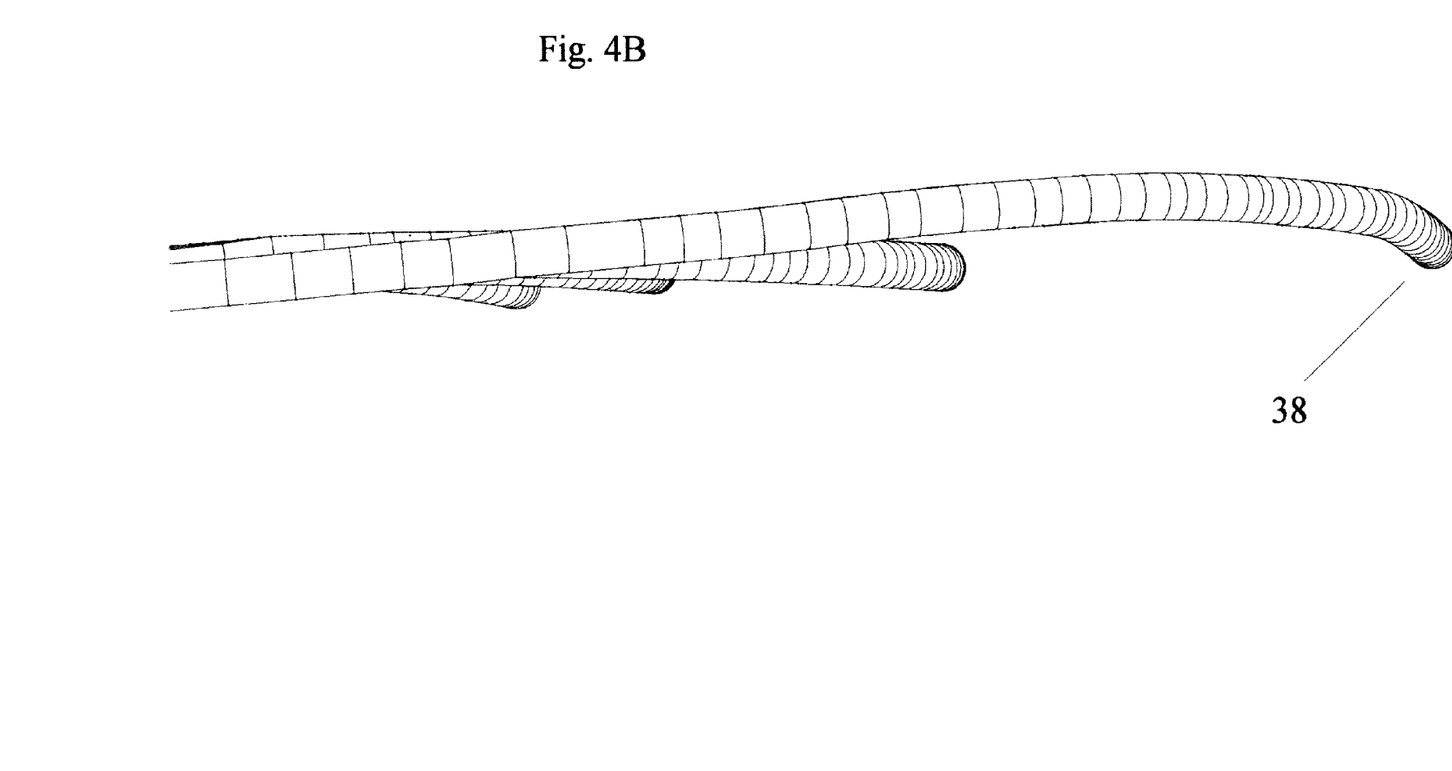
FIG. 4B is a view of just the lower portion of the copper tubing from the side.
Figure 4C:
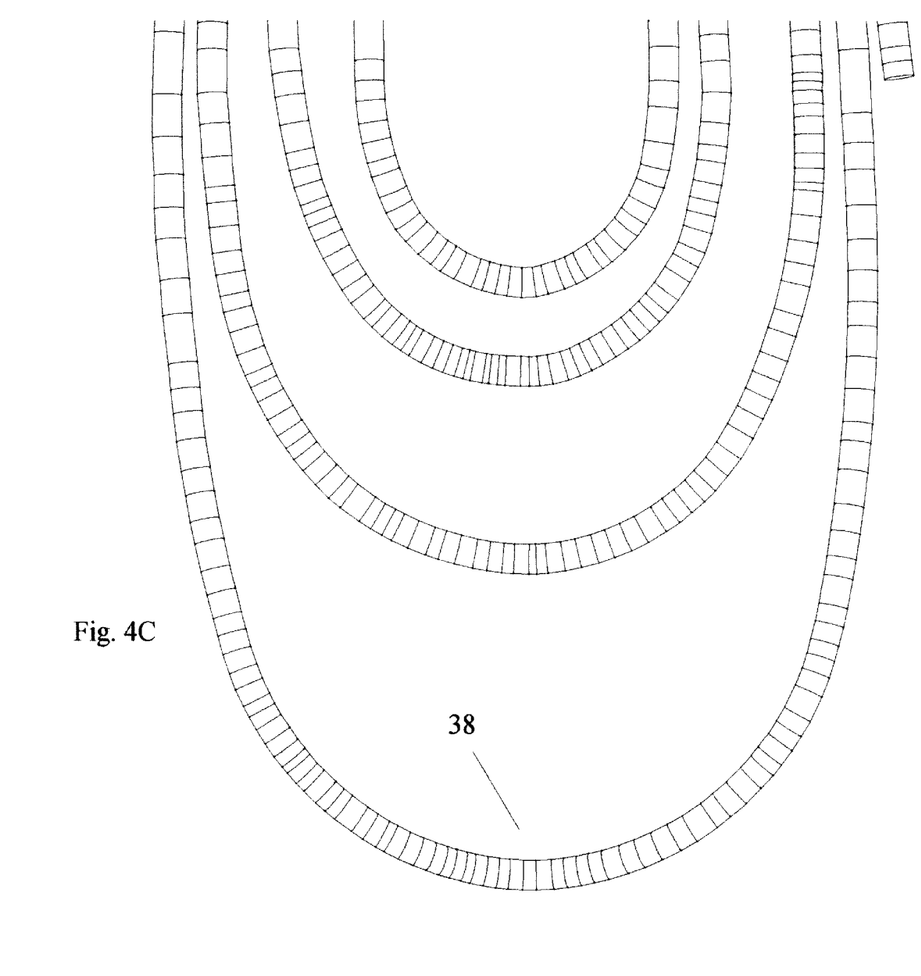
FIG. 4C is a view of just the lower portion of the copper tubing from directly above.
Figure 4D:
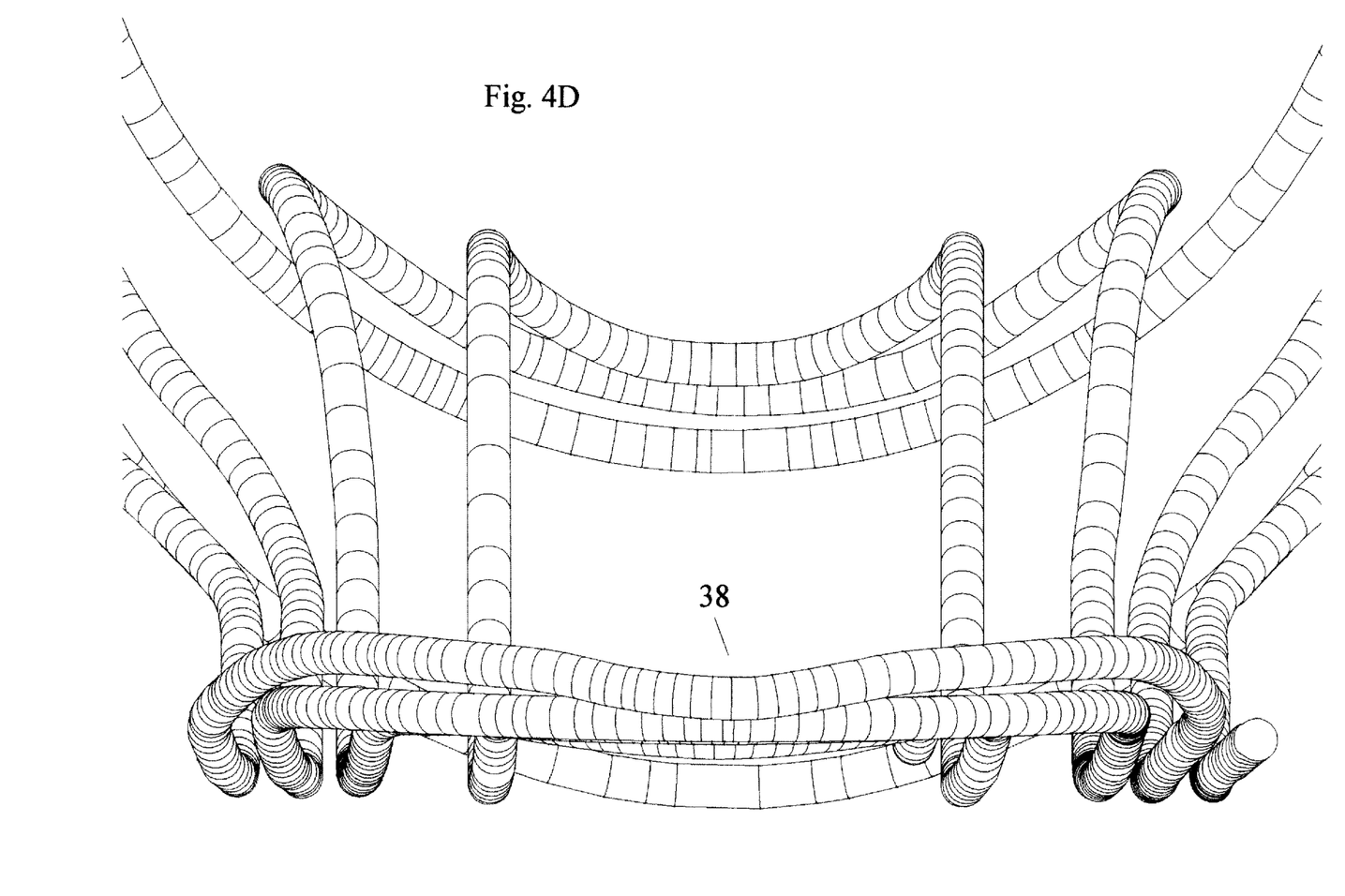
FIG. 4D is a view of just the copper tubing as seen while looking from the mid back portion, toward the neck portion.

FIG. 1 sample pattern piece 8 recessed area
10 extending portion

FIG. 2, 4A, 4B, 4C, 4D, 5A, and 5B 6 copper tubing
12 copper tubing inlet
14 copper tubing outlet
16 right side floating clip
18 left side floating clip
20 floating inner section
22 right side shoulder piece
24 right side neck piece
25 left side neck piece
26 left side head piece
27 right side head piece
28 right side neck floating inner section piece
30 left side shoulder piece
32 right side mid back piece
34 left side mid back piece
36 inner section inner piece
38 mid back 3D curve
44 outlet rubber tubing
46 inlet rubber tubing
60 left side neck floating inner section piece

FIG. 3 strap

DESCRIPTION

Understanding of the present invention and the various aspects thereof will be facilitated by reference to the accompanying drawing figures, submitted for purposes of illustration only and not intended to define the scope of the invention, on which:

FIG. 1 is a view from directly above a section of copper sheet metal as it would be cut out and look prior to bending its extending portions around the copper tube 6 of FIG. 2. The extending portions 10, are of a length that they would be able to wrap more than half way around the copper tube 6. The recessed area 8, are wide enough so as to allow the extending portions of a similar piece to inter lock through them around the same area of the tube. This pattern, FIG. 1, is to show extending portions as they appear before being wrapped around the tubing. The overall shape doesn't reflect an actual piece from the device.

FIG. 2 is a perspective view from the left side of a copper temperature controlled therapy device. A 3/16 inch copper tubing 6 makes a continuous unbroken line through the therapy device. This copper tubing forms the backbone of the device as it snakes back and forth to exit at the copper tubing outlet 14. The copper tubing is retained to its coiling shape by pieces of copper sheet metal 16, 22, 24, 25, 26, 27, 28, 30, 32, 34 and 60 that are cut to have extending portions that wrap around the tube as shown best by FIG. 1. These extending portions are positioned in such a way as to allow the opposing piece to link around the tube through each other. Thus the tubing is held to its shape by these interlocking pieces of copper sheet metal. More loosely floating copper hinge type pieces the right side floating clip 16 and the left side floating clip 18, hold the floating inner section 20 such that it is somewhat flexible. The right side floating clip 16 and the left side floating clip 18 use the same type of extending portions as depicted in FIG. 1.

As the copper tubing 6 begins its snaking pattern, starting in the center at the copper tubing inlet 12, it extends toward the left side head piece 26 and the right side head piece 27 where it then heads back to loop around the outside of the copper tubing inlet 12. After passing out side of the copper tubing inlet 12 it again heads back up to and loops around just inside of the left side head piece 26 and the right side head piece 27 then heads back down toward the right side mid back piece 32. These first two inner loops are held in position in relations to one another by the attachment of the left side neck floating inner section piece 60 and the right side neck floating inner section piece 28. The extending portions of the left side neck floating inner section piece 60 and the right side neck floating inner section piece 28 wrap around these two inner loops of the copper tubing 6 making them into a more stable unit. The recessed portions of the left side neck floating inner section piece 60 and the right side neck floating inner section piece 28 allow the extending portions of the inner section inner piece 36 to inter lock through them around the first inner loop of the copper tubing 6. The combination of the copper tubing 6, the left side neck floating inner section piece 60, the right side neck floating inner section piece 28, and the inner section inner piece 36 make up the inner floating section 20. The inner floating section 20 is loosely held in relation to the rest of the device by the right side floating clip 16 and the left side floating clip 18.

While the device is lying horizontally, the floating inner section 20 gradually curves upward from just to the left of, or below, the right side floating clip 16 and the left side floating clip 18. As this floating inner section 20 extends toward the right past the right side floating clip 16 and the left side floating clip 18 it begins to curve up more sharply. As it nears the location of the label 20, it begins to level off and curve back down toward the lower sections of the left side head piece 26 and the right side head piece 27. The inner most portion of the floating inner section 20, the inner section inner piece 36 doesn't have extending portions in its center, and doesn't have a section of tube to wrap around. It curves to follow the entire inner section length wise, and also curves somewhat downward crosswise. The inner section inner piece 36 completes the inner floating section 20 as a slightly dishing and curving channel that is also somewhat flexible within the inner floating section 20.

As the copper tubing 6 continues its path, it extends on down toward the top part of the bottom section and travels through the right side mid back piece 32 and the left side mid back piece 34 to complete the last part of the second loop. As the copper tubing 6 continues on, it passes through the middle of the left side floating clip 18, then to the inside of the left side shoulder piece 30. As it bends upwards in the left side shoulder piece 30, it shortly reaches the outside of the left side neck piece 25. At this point the left side shoulder piece 30 and the left side neck piece 25 are interlocked around the copper tubing 6 through each other. As the copper tubing 6 leaves the left side shoulder piece 30 it continues to loop over the top and back down to reenter the other side of the left side neck piece 25 and then to interlock with the inside of the left side head piece 26. As the copper tubing 6 continues looping down, and back toward the center, it leaves the left side headpiece 26 just before reaching the lowest point for this loop. Just past the lowest part of this loop, the copper tubing 6 enters the extending portions of the inside of the right side head piece 27 and shortly there after the right side neck piece 24. As the copper tubing 6 leaves the right side head piece 27 and the upper part of the right side neck piece 24 behind, it loops over the top of the right side neck piece 24, then enters the right side shoulder piece 22 and reenters the other side of the right side neckpiece 24. At this point, the right side shoulder piece 22 and the right side neckpiece 24 are interlocking around the copper tubing 6. Continuing on, the copper tubing 6 leaves the right side neckpiece 24, then the right side shoulder piece 22 curving on down to pass through the center of the right side floating clip 16. From the right side floating clip 16, the copper tubing 6 begins to level off, then enters the outside of the right side mid back piece 32 performs a 3D curve dip at the mid back 3D curve 38, then curves back around to enter the outside extensions of the left side mid back piece 34. Heading back toward the upper portions the copper tubing 6 passes through the outside of the left side floating clip 18, curves outwards a bit to enter the outside extensions of the left side shoulder piece 30. Leaving the left side shoulder piece 30, the copper tubing 6 loops over the top of itself and the left side neck piece 25, then heads down to enter the outside of the left side head piece 26. Curving around to leave the left side headpiece 26 it enters the outside of the right side headpiece 27 just past the bottom of the curve. Curving on around, the copper tubing 6 leaves the out side of the right side head piece 27 loops up over itself and the right side neck piece 24 then slopes back downward to enter the out side of the right side shoulder piece 22, then exits the right side shoulder piece 22. Curving downward the copper tubing 6 begins to level off as it passes through the outside of the right side floating clip 16 and comes to an end at the copper tubing outlet 14.

The lower skull pieces the left side head piece 26 and the right side head piece 27 continue the curve of the floating inner section 20 from 20 down to the same plan as the section just below the right side floating clip 16 and the left side floating clip 18, but only the bottom most portion of the section of tubing around the out side of the left side head piece 26 and the right side head piece 27 actually enters this plan. This leaves the left side head piece 26 and the right side head piece 27 at an angle to the plan of the right side floating clip 16 and the left side floating clip 18. As the left side headpiece 26 and the right side headpiece 27 extend downward from the floating inner section 20, they curve back towards the horizontal plan or to the right of the drawing. This leaves a dished area formed by the curving of the lower skull pieces the left side headpiece 26 and the right side headpiece 27.

The right side neck piece 24 and the left side neck piece 25 rise upward above the floating inner section 20 and curve inwards toward each other. The right side shoulder piece 22 and the left side shoulder piece 30 curve outward fairly sharply then back inwards a bit toward there top.

As the portion of the copper tubing that makes the outside loop through the bottom the mid back 3D curve 38, it also dips down slightly as it goes through the last portions of the right side mid back piece 32 then at the bottom at the mid back 3D curve 38 it makes a smooth little curve back upwards as it enters the left side mid back piece 34. Thus this section of tubing, as well as many others, is making a 3D curve not just horizontally through the x and y, but also downwards in the z axis.

A rubber hose the inlet rubber tubing 46 is routed under the floating inner section 20 were it proceeds under one side of the left side shoulder piece 30 to loop back around and attach to the input end of the copper tube 6 at the copper tubing inlet 12. Another rubber hose the outlet rubber tubing 44, loops around the bottom end of the device past the right side mid back piece 32, the mid back 3D curve 38, and the left side mid back piece 34 to hook to the output end of the copper tube 6 and end at the copper tubing outlet 14.

FIG. 3

FIG. 3 is a perspective view of an optional pressure adjustment strap that attaches to the Copper Neck Support FIG. 2 on the out side of the right side neckpiece 24. From the right side neckpiece 24 it continues down under the floating inner section 20, and under the top end of the inner section inner piece 36. From there it extends back up to the out side of the left side neckpiece 25. This strap attaches to the out side of the right side neck piece 24 and the left side neck piece 25 with hook and loop fasteners, namely Velcro®.

FIGS. 4A, 4B, 4C, and 4D

Figure 5A:
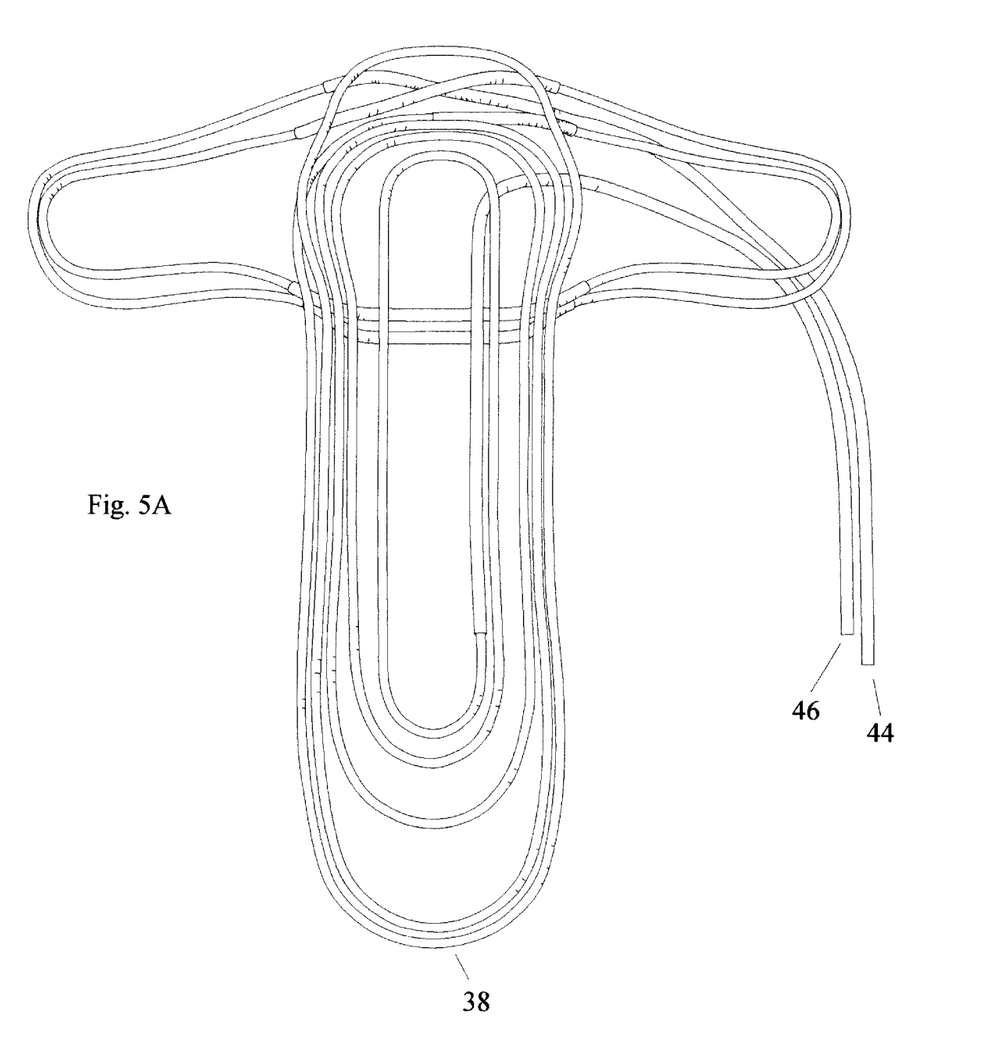
FIG. 5A is a view of just die tubing layout for a neck device with folding neck side sections, as is seen from directly above.
Figure 5B:
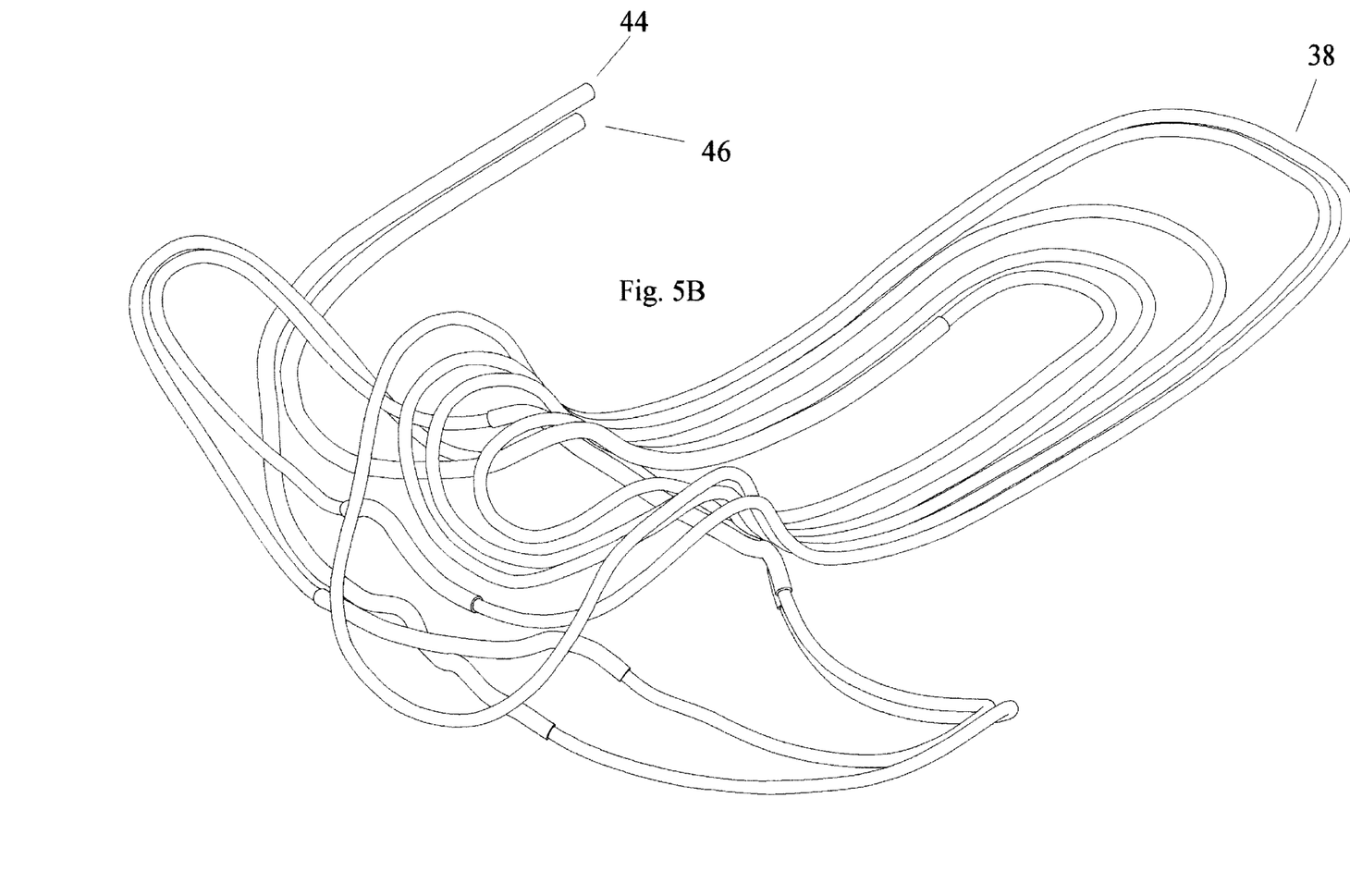
FIG. 5B is a North West isometric perspective view of just the tubing layout for a neck device with folding neck side sections.

FIGS. 4A, 4B, 4C, and 4D are of just the copper tubing, and are provided to assist with understanding of how the tubing of this device of this method would be shaped to provide the user with ergonomic support, while at the same time giving the vertebrae clearance.
FIGS. 5A, and 5B Reference to FIGS. 5A, and 5B will help the reader visualize how a device of this method designed with folding neck side pieces would work. One can see how a tubing configuration can be adapted for more repeated movement. Copper sheet metal pieces similar to those shown in FIG. 3 would bridge the space between the tubing as with FIG. 3, but would be arranged such as to allow the hinge type bending in necessary locations.

Operation

The implementation of this method is:
1) A coiled copper tubing and copper sheet metal device is placed next to and compared to the shape of the user's skin in the location to be treated. This to see if it's shape is suitable for the treatment desired;
2) If needed, adjustments are made and the device is left in, or secured in contact with the patient's skin;
3) Then a substance is circulated through the device to provide the desired temperatures.

To further assist with the understanding of this method, focus is directed more specifically to the operation of one of the devices used to implement this method, by providing a closer look at the operation of the device shown in the drawings in FIG. 2, the Copper Neck Support Device as described in the description and drawings, above. For the most effective relief of sore, aching, or traumatized necks while using this device, of this method, the best results are achieved by laying on ones back on a comfortable bed, though this device can be used sitting up, or even while walking. The Copper Neck Support FIG. 2 is slipped inside the users clothing next to the skin. The lower portions the mid back 3D curve 38 extends down to the users mid back, the right side shoulder piece 22 and the left side shoulder piece 30 sit on the users shoulders, while the floating inner section 20, the right side neck piece 24 and the left side neck piece 25 cradle the users neck. The left side headpiece 26 and the right side headpiece 27 reach up to the lower part of the users head. The mid back 3D curve 38 helps to provide for the knobby portions of the user's spine in much the same way that the gap in the middle of the inner section inner piece 36 provides for this. The user then lays back on the bed, or is placed on the device by attendants depending on the conditions requiring care, and the pressure adjustment strap, FIG. 3, is adjusted to fit the user most comfortably. If the treatment is to help increase the curve of the neck a little extra pressure may be added.

In this configuration, even without the cooling and or heating options hooked up or functioning, this device utilizing this method provides some relief and helps the user's muscles to relax. The therapeutic anti-inflammatory properties of copper in contact with and absorbing into the skin helps to reduce swelling and to relax muscles. While the curving flexible ergonomic design provides the neck with a bit of curving traction that helps to take the pressure off of the disks in between the vertebrae in the neck.

This device of this method provides further benefits if the device is hooked up to any of different types of temperature exchange systems mentioned in the prior art. When hooked up to a temperature exchange systems, fluid or gases are circulated into the device by entering the inlet rubber tubing 46 and from there into the device. As the temperature transporting substance travels through the tubing, it carries its temperature first to the inner portions of the device including the more sharply curved portion the floating inner section 20 that supports the back of the neck. From the inner portion it continues on to the outer portions including the right side neck piece 24, the left side head piece 26 the support for the lower portion of the head, and through the right side shoulder piece 22 as it leaves the copper tubing 6 exiting out through the copper tubing outlet 14. From the copper tubing outlet 14, the temperature transporting substance travels back out the outlet rubber tubing 44 to either be recirculated or disposed of in a drain. As the substance circulates, the temperature is conducted to the copper tubing 6, from the copper tubing 6 to the copper sheet metal pieces which carry the thermal properties of the substance traveling through the copper tubing 6 bridging the gap between the various portions of the copper tubing 6. This provides a more uniform temperature for the user.

Use of this device, of this method, without the optional strap can be preformed with a towel roll. This has some benefits for some conditions in that it raises the device a little higher putting less pressure on the back of the head. The inner portion of the device that extends to the back of the neck the floating inner section 20 is floating and flexible. Two short interlocking pieces, the right side floating clip 16 and the left side floating clip 18, are positioned such that they allow the inner portion above them to flex in and out. The inner section inner piece 36 is of copper sheet metal whose central portion is free floating and not wrapped around the tube. This floating section the inner section inner piece 36 allows the knobby portions of the users spine room to move without receiving as much pressure. The flexibility allows the user to position a towel roll under the floating inner section 20 and vary the amount of pressure on the back of the neck by the size that the towel roll is rolled up to. A smaller roll decreases the amount of pressure on the neck and increases the pressure on the head. Conversely, a larger roll increases the amount of pressure on the back of the neck and somewhat decreases the pressure on the back of the head while also providing a certain amount of curved traction to the neck. With use of the strap, FIG. 3, it is simply loosened or tighten as need, and maybe used with or with out the towel roll.

Operation—FIGS. 5A, and 5B

For a still further understanding of this method, attention is directed to another device for the implementation of this method as illustrated by FIGS. 5A and 5B of the drawings. By reference to the drawings one skilled in the art would recognize its advantages. A device of similar construction to FIG. 3, a coiled copper tubing and copper sheet metal construction, which is configured to better suit use of the device on users with traumatic injury. This device is designed so pieces similar to those shown in FIG. 2, the right side neck piece 24 and the left side neck piece 25, which can be easily swung outward, away from each other. This can be accomplished several different ways but is mainly to make application of the device to the user, primarily those on their backs, easier. For application to patients that are laying on their backs on a hard surface, the device could be of shorter construction, so that it does not extend as far down the patients upper back as does the device shown in FIG. 2. As would be apparent to those skilled in the art of the application of C-Spine Precautions, this reduces the amount of movement necessary to apply the device before application of other necessary components of C-Spine Precautions. The right side neck piece as similar to the one shown FIG. 2, 24 and the left side neck piece FIG. 2, 25 would be simply pivoted out of the way, as one attendant stabilizes the patients head, the other checks the shape of the device to see that it matches the curve of the back of the patients neck. Then the device is slipped into place under the patient's neck so that it is just in contact with the skin. To finalize the applications of the device, the right side neckpiece 24 and the left side neckpiece 25 are positioned or allowed to come in contact with the sides of the patient's neck. As one skill in the art would recognize, standard C-Spin precautions would then be administered leaving the rubber coolant tubes extending from the C-collar. As one skilled in the art would also recognize, to save time, this device could be attached adjustably to the correct location of the C-collar in advance by hook and loop fasteners or other attachment means. Then both devices could be slipped behind or under the patient's neck simultaneously. The device at the back of the neck would then be check for curve, the collar would be wrapped around as usual, and last the right side neck piece and the left side neck piece would be checked for alignment. Then the C-collar would be fastened, and as with other applications, the coolant substance would be circulated.

For still further understanding of the present invention, attention is directed to another device for the implementation of this method that is not shown in the drawings. A device of similar looped copper tubing and copper sheet metal construction, which is configured to better suit use of the device on users with an injured or hurting limb. Though this device, of this method, is not shown, by reference to the drawings one skilled in the art would recognize its advantages. The lower portions of FIG. 2 could be lengthened and utilized for treatment of the limbs. With the use of this device, in the implementation of this method, as with the other devices, the device is adjusted to the best shape suited for the limb and its current condition. The device is placed against the user's skin, and a temperature controlling substance is circulated through the device to provide the temperature best suited for the condition and treatment desired. In the cases of immobilization of a possible fractured, or sprained limb, a wrapping material may be wrapped around the limb and the device to further enhance immobilization stability. This also helps preserve the temperature of the substance traveling through the device and thus improve the ability of the device to provide the desired temperature.

Similarly, devices used in the implementation of this method can be covered with rubber on the side of the devices that face away from the user's skin. This rubber provides insulation to keep the device's temperature controlling substance from losing its temperature to this side. This rubber also facilitates cleaning of the devices by keeping undesirable substances out of the rougher areas on the backside while still allowing the devices to be adjusted to suit the desired application. In some areas, the rubber would provide for more flexibility by joining two or more assemblies of the copper tubing in areas where greater flexibility is desired. As with the case of a device better suited for C-Spine Precautions, an amount and hardness of rubber suited for enough rigidity to hold the neck side pieces in place, while still allowing them to flex out of the way has it's benefits.

CONCLUSION, RAMIFICATIONS, AND SCOPE

As one skilled in the art would see, though, not shown here, devices of similar construction for other areas of the body that are of such a design as to be conformable to those areas such as the lower back are also implemented by this method. Likewise, similar perhaps pre-dished pieces provide for control of temperature and energy around the user's head.

Accordingly, the reader will see that devices that utilize the combination of: copper in contact with the skin, the ability to control the device's temperature, and the ability to adjust the devices ergonomic shape, are within the scope of the current invention. While the above description contains many specificities, these should not be construed as limitations on the scope of the invention, but rather as an exemplification of preferred embodiments thereof. Many other variations are possible. A similar device for treatment of the arm and hand could be shaped to conform to the relaxed shape of the hand.

Thus the scope of the invention should be determined by the appended claims and their legal equivalents, rather than by the examples given.

What is claimed is:

1. A method of inflammation control and therapy that combines the use of copper in direct contact with the skin and hot, and or cold treatment, comprising:
   a. providing a coiled copper tubing and copper sheet metal device the surface of which can be thermally controlled from hot to cold;
   b. placing said coiled copper tubing and copper sheet metal device in direct contact with the skin;
   c. controlling said coiled copper tubing and copper sheet metal device so that the temperature of said coiled copper tubing and copper sheet metal device changes to provide desired treatment;
   whereby small amounts of copper absorbs into the skin, while simultaneously hot, and or cold treatment is administered to the same location of the skin, and
   whereby a more effective method of inflammation control and therapy is provided.

2. The method of claim 1 wherein said more effective method of inflammation control and therapy is becomes even more effective by being in combination with the ergonomic shape of said coiled copper tubing and copper sheet metal device.

3. The method of claim 1 wherein said more effective method of inflammation control and therapy is performed on a neck.

4. The method of claim 1 wherein said more effective method of inflammation control and therapy is performed on a limb.

5. A device for inflammation control and therapy comprising:
   a. a bent and coiled copper tubing which is looped back and forth to conform to the shape of an area for which treatment is desired, and also, by nature, said bent and coiled copper tubing provides a cavity through which a thermal transporting substance may be circulated as desired;
   b. pieces of copper sheet metal cut to bridge across open spaces between said bent and coiled copper tubing while providing narrow elongated extensions on said pieces of copper sheet metal for interlocking through opposing said pieces of copper sheet metal around said bent and coiled copper tubing;
   whereby the combination of said bent and coiled copper tubing and said pieces of copper sheet metal form a copper device with improved thermal collector capabilities, which while used in direct contact with the skin, also provides a means for small amounts of copper to be absorbed into the skin, and a means for electrons to be exchanged with the skin; and,
   whereby said copper device provides improved means of inflammation control and therapy.

6. The device of claim 5, where the shape of said copper device's is adjustable.

7. The device of claim 5, where the shape of said copper device is ergonomic.

8. The device of claim 5, where said copper device is coated with rubber on one side so that the rubber is not between the device and the patient.

9. The device of claim 5, where said copper device is for the treatment of a neck.

10. The device of claim 5, where said copper device is for the treatment of a limb.

11. The device of claim 5, where said copper device is for the treatment of a head.

12. The device of claim 5, where said copper device is for the treatment of a back.

13. The device of claim 5, where said copper device is ergonomic and adjustable.

14. The device of claim 13, where said copper device is coated with rubber on one side so that the rubber is not between the device and the patient.

15. The device of claim 13, where said copper device is designed for treatment of a neck.

16. The device of claim 13, where said copper device is for treatment of a limb.

17. The device of claim 13, where said copper device is for the treatment of a back.

18. The device of claim 13, where said copper device is for the treatment of a head.

19. A device for inflammation control and therapy of a human's upper back, neck and lower skull comprising:
   a. a bent and coiled copper tubing which is looped back and forth to ergonomically conform to the shape of said human's upper back, said neck and said lower skull,
   b. pieces of copper sheet metal cut to bridge across open spaces between said bent and coiled copper tubing while providing narrow elongated extensions on said pieces of copper sheet metal for interlocking through opposing said pieces of copper sheet metal around said bent and coiled copper tubing;
   c. two outwardly extending assemblies of curved and bent copper tubing and said pieces of copper sheet metal ergonomically contoured to the sides of said neck;
   d. rubber as a interconnection means for circulating thermal transporting fluid through said bent and coiled copper tubing, through said two outwardly extending assemblies, and out of said device, and the said rubber thereby providing a means for said two outwardly extending assemblies to fold down away from said sides of said neck;
   e. and said rubber thereby providing a means for said thermal transporting fluid to control the temperature of said outwardly extending portions, of said bent and coiled copper tubing, and of said pieces of copper sheet metal;
   whereby said device provides improved means of inflammation control and therapy of said human's back, said neck and said lower skull.

20. The device of claim 19, wherein said device is combined with molded rubber or plastic material, thereby said molded rubber or plastic material provides: a smoother surface for ease of cleaning, an improved feel, and also thereby insulation to reduce unproductive thermal loss.

21. A device for inflammation control and therapy of a human's limb comprising:
   a. a bent and looping copper tubing which is looped back and forth to ergonomically conform to the shape of said human's limb,
   b. pieces of copper sheet metal cut to bridge across open spaces between said bent and looping copper tubing while providing narrow elongated extensions on said pieces of copper sheet metal for interlocking through opposing said pieces of copper sheet metal around said bent and looping copper tubing;
   c. rubber as a interconnection means for circulating thermal transporting fluid through said bent and looping copper tubing, and out of said device;
   whereby said device provides improved means of inflammation control and therapy to a said human's limb.

22. The device of claim 21, wherein said device is combined with molded rubber or plastic material, thereby said molded rubber or plastic material provides: a smoother surface for ease of cleaning, an improved feel, and also thereby insulation to reduce unproductive thermal loss.

* * * * *